United States Patent [19]

Bartels-Keith et al.

[11] Patent Number: 4,503,139
[45] Date of Patent: Mar. 5, 1985

[54] PHOTOGRAPHIC PRODUCTS AND PROCESSES AND NOVEL COMPOUNDS

[75] Inventors: James R. Bartels-Keith, Lexington; Roger A. Boggs, Wayland; Anthony J. Puttick, Arlington; Nancy M. Sofen, Cambridge, all of Mass.

[73] Assignee: Polaroid Corporation, Cambridge, Mass.

[21] Appl. No.: 492,695

[22] Filed: May 9, 1983

[51] Int. Cl.$^3$ .............. G03C 5/54; G03C 1/10; G03C 1/30; G03C 1/40
[52] U.S. Cl. .................. 430/219; 430/212; 430/218; 430/251; 430/542; 430/543; 430/544; 430/559; 430/564; 430/611; 430/614; 430/955; 430/957; 430/959; 430/960
[58] Field of Search ............ 430/212, 218, 219, 251, 430/443, 544, 566, 614, 611, 955, 957, 959, 960, 564, 559, 543, 542

[56] References Cited

U.S. PATENT DOCUMENTS

| | | | |
|---|---|---|---|
| 3,255,202 | 6/1966 | Johnson | 430/614 |
| 3,271,154 | 9/1966 | Dersch et al. | 430/614 |
| 3,353,956 | 11/1967 | Rogers et al. | 430/218 |
| 3,667,957 | 6/1972 | Willems et al. | 430/614 |
| 3,698,898 | 10/1972 | Grasshoff et al. | 430/219 |
| 3,719,489 | 3/1973 | Cieciuch et al. | 430/222 |
| 4,126,459 | 11/1978 | Greenwald | 430/251 |
| 4,350,752 | 9/1982 | Bartels-Keith et al. | 430/219 |
| 4,350,754 | 9/1982 | Reczek et al. | 430/219 |
| 4,363,865 | 12/1982 | Reczek et al. | 430/223 |

FOREIGN PATENT DOCUMENTS 1584113 2/1981 United Kingdom .

Primary Examiner—Richard L. Schilling
Attorney, Agent, or Firm—Gaetano D. Maccarone

[57] ABSTRACT

There are described novel photographic products and processes which utilize compounds which release a photographic reagent in the presence of alkali. The compounds include an imidazole blocking group and cleave in alkali to release the photographic reagent. Also described are novel compounds.

26 Claims, 1 Drawing Figure

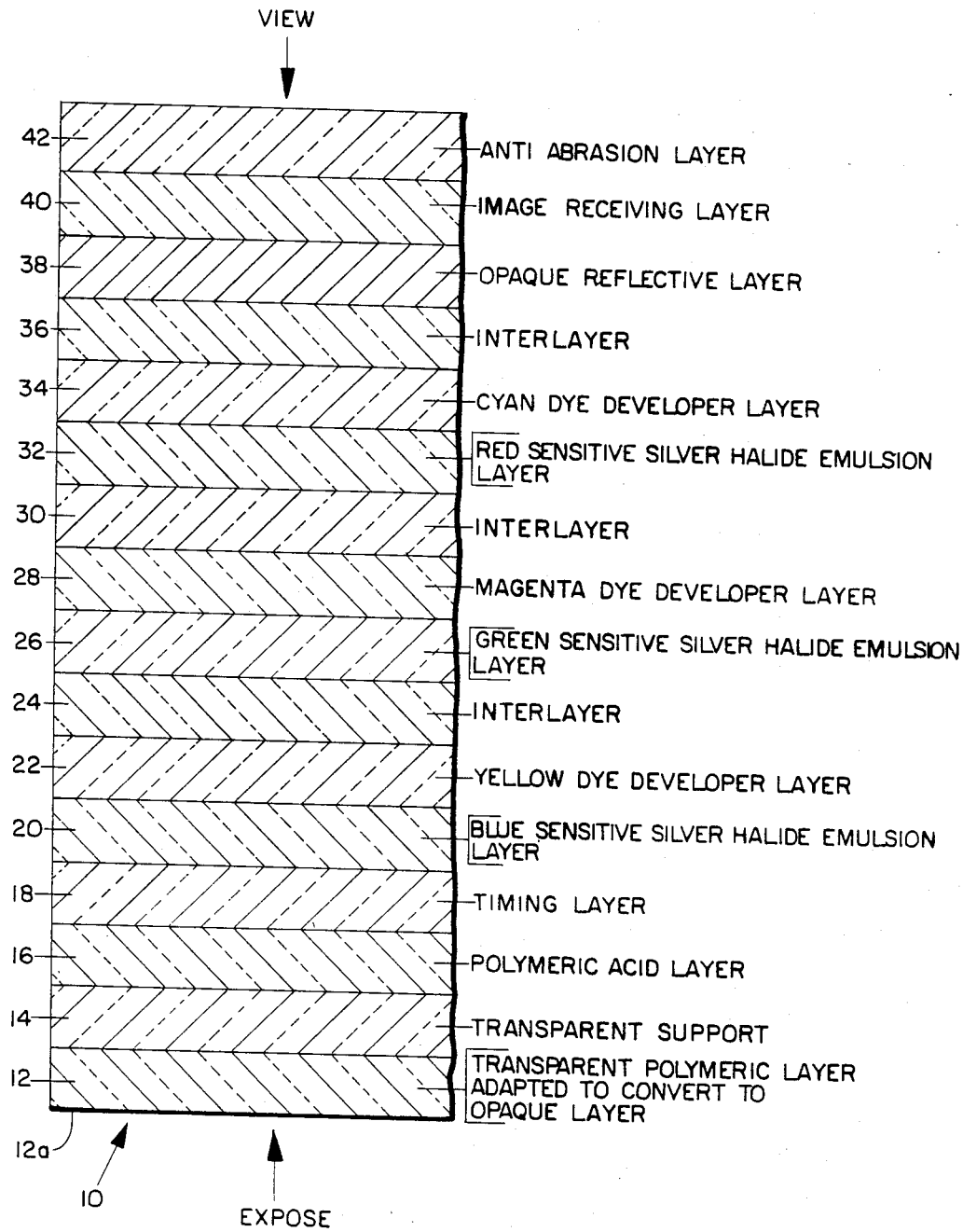

PHOTOGRAPHIC PRODUCTS AND PROCESSES AND NOVEL COMPOUNDS

BACKGROUND OF THE INVENTION

In various photographic systems for forming images, whether in black and white or in color, it is often desirable to include in the photographic film unit one or more of the various photographic reagents required for development and/or to enhance image quality. This practice extends both to conventional systems for forming negative images and also to various systems such as diffusion transfer wherein a positive image in silver or in color is obtained.

In many instances, the photographic reagent may be contained initially in either the processing composition applied for development and image formation or in the film unit itself. The latter is typically preferred so as to reduce the number of ingredients required in the processing composition.

In other instances, the particular photographic reagent desired is not sufficiently stable in alkali to provide the requisite shelf life for the processing composition or the reagent is incompatible and/or reacts with another reagent in the processing composition and therefore must be contained initially in the film unit.

In still other instances, the reagent must be provided at some particular time in the development process which requires that it be present in a specified layer or in specified proximity to another layer in the film unit.

In all of the foregoing instances, it is desirable that the reagent be contained in the desired layer or layers of the film unit in a form that is stable and non-migratory or non-diffusible and yet available when it is required at a particular time in the development process. To accomplish this result, it is known in the art to attach to the particular photographic reagent a blocking moiety which prevents the photographic reagent from reacting with other photographic materials present in the film unit or migrating or diffusing prior to the time when photographic development is effected but which will release the photographic reagent at the desired time such as by reaction with the aqueous alkaline processing composition.

The present application relates to photographic products and processes which utilize compounds which release a photographically useful reagent in the presence of alkali and to novel compounds.

SUMMARY OF THE INVENTION

It is therefore an object of this invention to provide novel compounds.

It is another object to provide compounds which are useful in photographic applications.

A further object is to provide compounds which provide controlled release of a photographically useful reagent during development of an exposed photosensitive element.

Another object is to provide compounds which provide controlled release of a development restrainer during development of an exposed photosensitive element.

Still another object is to provide compounds which provide a controlled release of a gold transfer agent during development of an exposed photosensitive element.

Yet another object of the invention is to provide photographic products and processes utilizing such compounds.

BRIEF SUMMARY OF THE INVENTION

These and other objects and advantages are accomplished in accordance with the invention by providing photographic products and processes which utilize compounds represented by the formula

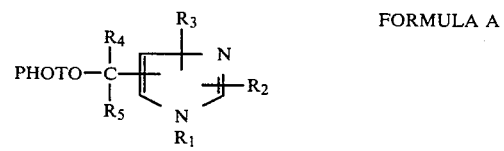

FORMULA A wherein
$R_1$ is hydrogen, a hydrolyzable group or a group which is cleavable in aqueous alkaline environment;

$R_2$ and $R_3$ may be the same or different and may be hydrogen or any substituent which modifies a property of the compound such as, for example, its solubility, mobility or diffusibility, or the release rate of the PHOTO moiety in alkali; or when the $$\begin{array}{c} R_4 \\ | \\ -C-PHOTO \\ | \\ R_5 \end{array}$$

substituent is attached to the 2 position of the imidazole ring, $R_2$ and $R_3$ taken together with the carbon atoms of the imidazole ring to which they are attached may form a five or six member carbocyclic ring or heterocyclic ring including one or more heterocyclic atoms such as nitrogen, sulfur or oxygen;

$R_4$ and $R_5$ may be the same or different and may be hydrogen or alkyl, preferably having from 1 to 6 carbon atoms; and PHOTO represents the photographic reagent residue; or a photographically acceptable acid addition salt thereof.

It should be understood that various of the compounds structurally depicted in this application may exist in more than one tautomeric form and the structural formulas which appear herein are intended to encompass all tautomeric forms of the compounds encompassed thereby.

The $$\begin{array}{c} R_4 \\ | \\ -C-PHOTO \\ | \\ R_5 \end{array}$$

substituent may be attached to the imidazole ring in the 2, 4 or 5 positions. Thus, compounds within Formula A may be represented by the following formulas:

![Formula B structure]

FORMULA B and

-continued

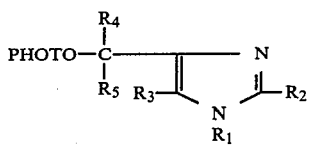
FORMULA C

Typical hydrolyzable groups which are suitable for use as $R_1$ include, for example, acyl groups such as acetyl or benzoyl, ester groups such as

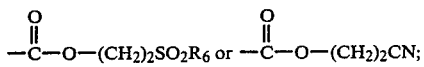

where $R_6$ is alkyl, preferably having from 1 to 6 carbon atoms, or aryl such as phenyl; and —$CH_2$—$CH_2$—Y, where Y is —CN,

or —$SO_2R_6$.

Typical groups which are cleavable in aqueous alkaline environment and which are suitable for use as $R_1$ include those which are cleavable by hydrolysis; those which cleave by quinone methide elimination such as are disclosed in U.S. Pat. No. 3,698,898, e.g., $R_1$ is

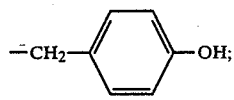

those which cleave by hydrolysis followed by quinone methide elimination, e.g., $R_1$ is

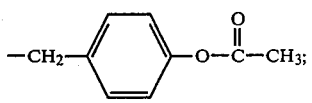

and those which cleave by β-elimination, e.g. $R_1$ is —$CH_2$—$CH_2$—CN,

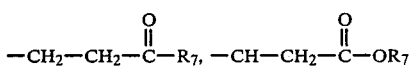

where $R_7$ is alkyl;

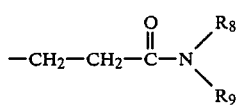

where $R_8$ and $R_9$ are H or alkyl; or —$CH_2$—$CH_2$—$SO_2R_{10}$ where $R_{10}$ is alkyl or aryl.

As stated above $R_2$ and $R_3$ may be hydrogen or any substituent which modifies a property of the compound such as solubility, mobility or diffusibility, or release rate. Thus, $R_2$ and $R_3$ may be short chain alkyl groups, e.g. those having from 1 to about 9 carbon atoms, or aryl such as phenyl; or solubility-affecting groups such as, for example, carboxylic acid, hydroxyethyl, alkoxy, carboxamide, and the like; or mobility-or diffusibility- affecting groups which may be expressed as ANCHOR which represents an anchoring or ballasting substituent such as alkyl having at least 10 carbon atoms, e.g., decyl, dodecyl, stearyl, oleyl, etc., which may be linked directly to the imidazole ring or indirectly through an appropriate linking group such as a —CONH—, alkylene —CONH— or

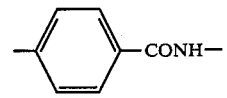

group; a polymeric substituent, e.g., a high polymer backbone; a plurality of short chain radicals which together provide the anchoring moiety; or an aromatic ring, e.g., of the benzene or naphthalene series, or a heterocyclic ring, which rings may be bonded to a single carbon atom of the imidazole ring; or as described previously $R_2$ and $R_3$ together may form a carbocyclic or heterocyclic ring fused to the imidazole nucleus.

PHOTO may be any of many photographic reagents such as development restrainers, e.g., mercaptoazoles, silver halide solvents, e.g., sodium and potassium thiosulfates and thiocyanates; toning agents such as thioureas and substituted thioureas; antifoggants; inorganic silver halide developing agents, e.g., sodium dithionate; and organic silver halide developing agents, e.g., those of the dihydroxybenzene, diaminobenzene or aminophenol series. Many of each of these types of photographic reagents are well known to those skilled in the art and therefore extensive discussion of specific suitable photographic reagents is not required here.

The compounds within Formula A, B and C cleave in alkaline compositions to provide a controlled release of the photographically useful reagent. The imidazole moiety of the compounds provides a timed release of the photographic reagent in the alkaline environment typically encountered in the processing of photographic elements and particularly where the alkaline medium has a relatively high pH, e.g., in the range of from about 12 to about 14. The rate of release of the photographic reagent is dependent upon the hydroxyl ion concentration and therefore the rate of release increases as the pH increases. The cleavage reaction in alkali occurs according to the following sequence, for example,

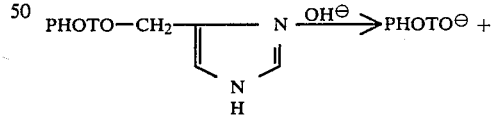

It should be noted here that the imidazole residue, such as the hydroxymethylimidazole illustrated above, may react further in the alkaline composition to form other products.

The rate of release of the PHOTO moiety is also temperature dependent, i.e., it is released at a rate which increases with the temperature at which processing of the film unit is effected. Thus, more of the photographic reagent is made available at elevated temperatures, i.e., above room temperature, less is released at room temperature and even less below room temperature. Thus, the compounds which are utilized according to the invention can provide more uniform sensitometry for the film units of the invention over a wide temperature range of processing. In other words, the sensitometry of the film units which include such blocked compounds according to the invention can be less temperature dependent than would otherwise be the case.

In a preferred embodiment of the invention the compounds are utilized to release a development restrainer during development of an exposed photosensitive element. In a particularly preferred embodiment where PHOTO is a development restrainer, PHOTO can be represented as

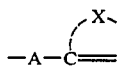 or 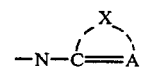

FORMULA D    FORMULA E wherein A is sulfur or selenium and X represents the nonmetallic atoms necessary to form a nucleus which completes a five or six member heterocyclic moiety including substituted rings and fused rings. These compounds cleave in alkaline compositions to provide mercaptoazoles which are diffusible in aqueous alkaline processing compositions. As stated previously the heterocyclic moiety includes substituted rings and fused rings. Where the heterocyclic azole moiety is substituted, the substituents(s) may be attached to either a nitrogen atom or a carbon atom of the azole moiety. The preferred heterocyclic rings with Formulas D and E include groups wherein the heterocyclic atoms, i.e., atoms other than carbon, are members of a single heterocyclic ring rather than fused or condensed heterocyclic rings wherein the heterocyclic atoms are members of more than one heterocyclic ring. The development restrainer moieties within Formulas D and E include monoazoles such as benzoxazoles, benzothiazoles, etc.; imidazoles; triazoles such as 1,2,4-triazoles, benzotriazoles, etc.; tetrazoles and pyrimidines. The most preferred heterocyclic moieties within Formulas D and E are tetrazoles and a particularly preferred ring is a phenyl substituted tetrazole which may also be substituted on the phenyl ring.

As discussed previously, the rate of release of the photographic reagent from the compounds of the invention is dependent upon the hydroxyl ion concentration of the aqueous alkaline environment and also upon temperature. In addition, the compounds wherein PHOTO is a development restrainer moiety within Formula D and E release the restrainer moiety at varying rates dependent upon where the blocking group is attached to the azole moiety, i.e., whether the blocking group is attached to a sulfur or selenium atom on the one hand or to a nitrogen atom on the other and also upon electrostatic effects brought about by the ionization of atoms in the molecule upon contact with an aqueous alkaline medium which could reduce the rate at which the release mechanism occurs. Such variables permit the selection of a compound having release rates desired for a particular application.

When incorporated into a photographic element, these blocked development restrainers permit initial development to occur normally during processing of the element with an aqueous alkaline processing composition and then undergo cleavage to restrain or control further development. Upon cleavage of the molecule the heterocyclic ring taken together with the sulfur or selenium atom provides a silver halide development restrainer. As mentioned above, the blocking moiety provides a timed release, i.e., release after a predetermined time, of the development restrainer moiety in the alkaline environment encountered during photographic processing. When the heterocyclic azole moiety is substituted with a phenyl ring, the latter may be attached to a nitrogen atom or to a carbon atom of the ring.

A preferred group of compounds according to the invention are those wherein the azole moiety is represented by either of the formulas

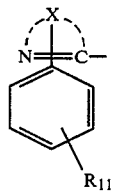

FORMULA F

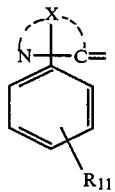

FORMULA G wherein $R_{11}$ is either a group which has a pKa of from about 7 to about 14, preferably at least about 8.5 or higher, which is ionizable to an anion whereby the silver salt of the moiety resulting from cleavage of the blocking group is more soluble in the pH range within which $R_{11}$ is ionized to an anion than it is below that pH range, or a precursor of such a group. Typical substituents which are useful as $R_{11}$ include: OH;

$$-\overset{O}{\underset{\parallel}{C}}-CH_3; \quad -O-\overset{O}{\underset{\parallel}{C}}-CH_3;$$

$-SO_2NH_2$; $-SO_2NHCH_3$; $-SO_2NHC_8H_{17}$; $-NHSO_2CH_3$;

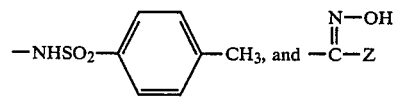

where Z is H, alkyl having from 1 to 10 carbon atoms, aralkyl such as benzyl or phenethyl, phenyl or substituted phenyl. Upon cleavage of the molecule as described above, there is provided a photographically useful material which provides desirable results such as will be described in detail below herein.

As stated above, $R_{11}$ may also be a precursor of a substituent which has the requisite properties and the desired substituent may be formed in situ. For example, it is possible to incorporate in the film unit as a precursor a compound having an azole moiety within Formulas F or G which has a hydrolyzable ester group on the phenyl ring and generate the desired hydroxy group in situ during photographic processing. It should be noted here that the acetyl group which can be substituted on the phenyl ring does not ionize to any appreciable extent to form an anion in an aqueous alkaline processing composition. However, the presence in a film unit of a compound having an azole moiety within Formula F or G having an acetyl group substituted on the phenyl ring can provide advantageous results. It would appear that the compound undergoes a change in aqueous alkaline processing composition and that the acetyl substituent is a precursor of a group which has the requisite properties described above which provide the desired results.

In another preferred embodiment PHOTO is a thiourea or a substituted thiourea which is represented by the formula $$(HZ)_a \cdot R_{12}N\diagdown \atop R_{13}\diagdown N \diagdown C-S- \atop R_{14}\diagup \phantom{N}$$ FORMULA H wherein $R_{12}$, $R_{13}$ and $R_{14}$ may be the same or different and may be hydrogen, alkyl, preferably having from 1 to 6 carbon atoms, aryl such as phenyl, acyl such as acetyl or benzoyl, amino or amino substituted with alkyl having from 1 to 6 carbon atoms; Z is a photographically acceptable anion such as chloride, a naphthalene sulfonate such as 2-naphthalene sulfonate, tetraphenyl borate, etc.; and a is 0, 1 or 2.

BRIEF DESCRIPTION OF THE DRAWING

For a better understanding of the invention as well as other objects and further features, thereof, reference is made to the following detailed description of various preferred embodiments thereof taken in conjunction with the accompanying drawing wherein the FIGURE is a partially schematic cross-sectional view of one embodiment of a film unit according to the invention.

DESCRIPTION OF THE PREFERRED EMBODIMENTS

Preferred compounds according to the invention include those represented by the formula (I)

(II)

(III)

(IV)

(V)

(VI)

(VII)

(VIII)

(IX)

(X)

(XI)

(XII)

(XIII)

CH₂=CHCH₂N\
        C—S—CH₂—[imidazole].2HCl
CH₂=CHCH₂N/
        H (XIV)

[phenyl-tetrazole]—S—CH₂—[imidazole]

The compounds of the invention may be prepared by reactions which are well known in the art and these will be readily apparent to those skilled in the art, particularly in view of the specific examples which appear below herein.

Generally, the PHOTO compound is reacted with an appropriate imidazole such as a halomethylimidazole or its acid salt in a solvent in the presence of other appropriate materials dependent upon the particular compound desired. According to a preferred technique for forming compounds within Formulas A, B and C wherein PHOTO is an azole moiety within Formula D and E, the azole compound, for example, phenylmercaptotetrazole, is reacted with an appropriate imidazole such as 4-chloromethylimidazole hydrochloride in a solvent such as dimethylformamide in the presence of two equivalents of a base such as di-isopropylethylamine at a temperature of from 0°–40° C. Alternatively, an alkali metal salt of the azole compound could be reacted with the appropriate imidazole compound in a solvent in the presence of one equivalent of base. Where it is desired to have one or more substituents on the imidazole moiety in the final compound, an appropriately substituted 2- or 4-chloromethylimidazole compound can be used.

Similarly, compounds within Formulas A, B and C wherein PHOTO is a thiourea or substituted thiourea within Formula H can be prepared by reacting thioureas with halomethylimidazoles or their acid addition salts in a suitable solvent such as dimethylformamide at a temperature in the range of from about 20° to about 100° C.

The starting materials are commercially available in many cases and generally can be made by reactions which are known to those of ordinary skill in the art. For example, 2-mercaptoimidazoles can be prepared by the reactions disclosed in the Chemistry of Heterocyclic Compounds Vol. 6: Imidazole and Its Derivatives, Part I, HOffman, Interscience Publishers, Inc., New York, 1953, pages 77–85; hydroxyalkylimidazoles, ibid, pages 99–104; chloroalkylimidazoles, ibid, pages 121; mercaptothiazoles and mercaptobenzothiazoles can be prepared according to the methods disclosed in The Chemistry of Heterocyclic Compounds Vol. 34: Thiazole and Its Derivatives, Part I, Metzger, John Wiley and Sons, 1979, pages 260–269; Part 2, pages 370–377; benzoxazolethiazones can be prepared according to the methods disclosed in Heterocyclic Compounds, Vol. 5, Elderfield, John Wiley and Sons, 1957, pages 439–444; 5-mercapto-1,3,4-oxadiazoles can be prepared according to the methods disclosed in Heterocyclic Compounds, Vol. 7, Elderfield, John Wiley and Sons, 1961, page 352; mercapto-1,3,4 thiadiazoles, ibid, pages 587–612; and tetrazoles by the techniques disclosed in Heterocyclic Compounds, Vol. 8, Elderfield, John Wiley and Sons, 1967, pages 1–107. Mercapto-1,2,4-triazoles can be prepared by known literature techniques as described, for example, in J. Chem. Soc. E. Hoggarth 1163 (1949). The selenazoles may be prepared by similar techniques.

The release kinetics in solution of the compounds of the invention vary over a wide range. The $t_{\frac{1}{2}}$ times in solution, i.e., the time required for one-half of the material to undergo cleavage with release of the particular PHOTO moiety, for some of the compounds illustrated above are shown in Table I.

TABLE I

| COMPOUND | $t_{\frac{1}{2}}$ (SECONDS) |
|---|---|
| I | 0.018[1] |
| II | 0.0218[2] |
| III | 0.0126[1] |
| IV | 1.07[3] |
| V | 0.21[4] |
| VIII | 0.044[4] |
| X | 1.35[4] |
| XI | 18.7[5] |

[1] obtained using 1 × 10⁻⁴ molar concentrations in 30% acetonitrile/0.25 N aqueous potassium hydroxide solution at a temperature of 22° ± 0.1° C.
[2] obtained using a 5.33 × 10⁻⁴ molar concentration in 1% acetonitrile/0.01 N aqueous potassium hydroxide solution at a temperature of 22° ± 0.1° C.
[3] obtained using a 5 × 10⁻⁵ molar concentration in water/0.5 N potassium hydroxide at a temperature of 22° ± 0.1° C.
[4] obtained using a 1 × 10⁻⁴ molar concentration in water/1.0 N potassium hydroxide at a temperature of 22° ± 0.1° C.
[5] obtained using a 1 × 10⁻⁴ molar concentration in water/0.5 N potassium hydroxide at a temperature of 22° ± 0.1° C.

The compounds of the invention may be present in photographic elements in any appropriate location and in any amount which is required to accomplish their intended purpose. The amount necessary in any particular instance is dependent upon a number of factors such as, for example, the compound utilized, the type of photographic element, the location of the compound in the photographic element and the result desired. Routine scoping tests may be used to ascertain the concentration appropriate for any given photographic element. In a preferred embodiment of the invention the compounds are incorporated in diffusion transfer photographic film units as will be discussed in more detail below herein. In such film units the compounds may be incorporated in the photosensitive element and/or the image-receiving element or in a cover sheet.

The compounds of the invention may be utilized in any photographic system wherein the release of a photographic reagent during development of an exposed photosensitive element is desired, including photographic systems for forming images in black and white or in color and those wherein the final image is a silver image or one formed by other image-forming materials. Further, where appropriate, the compounds may be utilized in various layers of a multilayer photographic system in varying concentrations to ensure the desired distribution of the photographically useful reagent during processing.

The advantageous results which can be obtained through the use of a preferred species of the compounds according to the invention, i.e., those wherein the PHOTO moiety is an azole compound having a substituted phenyl substituent as shown in Formulas F and G are not completely understood. However, to further aid those skilled in the art to understand and practice that species of the invention, the proposed theoretical mechanism by which the advantageous results are thought to be effected will be discussed here. It should be understood, however, that the diffusion transfer photographic system has been proved to be operative and highly effective through extensive experimentation and the proposed theoretical mechanism is not to be construed as being limiting of the invention.

It is theorized that such advantageous results are obtainable because the compounds which are released as a result of the cleavage of the blocking moiety during processing perform different functions at different stages of the development process, that is, as weak silver solvents and promoters of development at one stage of the development process and as development restrainers, or inhibitors, at another stage of the process, and that the dual functions of these compounds within the diffusion transfer photographic system are pH dependent.

It is well known that in the diffusion transfer development process the pH of any particular location within the film unit varies with time. Typically, the processing composition employed in the process has a very high pH, e.g., from about 13-14 and during the development process each layer of the multilayer film unit goes through a broad pH range which includes very high pH levels and relatively low pH levels. When the pH is substantially equal to or above the pKa of the substituent $R_{11}$ on the phenyl ring, the dianion is formed, for example,

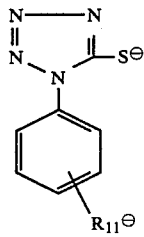

and acts as a weak silver solvent to form relatively soluble silver salts, thus promoting development. When the pH falls below the pKa of the substituent $R_{11}$, the monoanion is formed, for example,

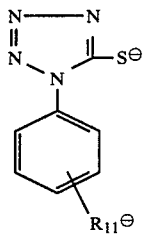

and the silver salt of the monoanion of the compound is very low in solubility resulting in a development restrainer action.

In view of the foregoing, it will be understood that when it is desired to utilize both functions, development of the exposed photosensitive element in the presence of such compounds is carried out with a processing composition having a pH substantially equal to or above the pKa of the particular substituent, at least for some period of time, when the processing composition comes into contact with the compound so as to enable the blocking moiety to cleave and the substituent ($R_{11}$) to ionize to form the dianion. In addition, at some point during the development process, the pH of the environment where the compound is located will go below the pKa of the substituent so as to enable the monoanion to be formed again. Of course, if it is desired to utilize only the development restrainer effect a processing composition having a pH lower than the pKa of the substituent could be used.

The compounds utilized according to the invention may be used in conjunction with any photographic emulsion. In a preferred embodiment the compounds are utilized in diffusion transfer photographic systems, particularly those which include a negative working silver halide emulsion, i.e., one which develops in the areas of exposure. Further, these compounds may be used in association with any image dye-providing materials. In a particularly preferred embodiment the diffusion transfer photographic film elements of the invention include one or more image dye-providing materials which may be initially diffusible or nondiffusible. In diffusion transfer photographic systems the image dye-providing materials which can be utilized generally may be characterized as either (1) initially soluble or diffusible in the processing composition but which are selectively rendered nondiffusible imagewise as a function of development; or (2) initially insoluble or nondiffusible in the processing composition but which selectively provide a diffusible product imagewise as a function of development. The image dye-providing materials may be complete dyes or dye intermediates, e.g., color couplers. The requisite differential in mobility or solubility may be obtained, for example, by a chemical reaction such as a redox reaction, a coupling reaction or a cleavage reaction. In a particularly preferred embodiment of the invention the image dye-providing materials are dye developers which are initially diffusible materials. The dye developers contain, in the same molecule, both the chromophoric system of a dye and a silver halide developing function as is described in U.S. Pat. No. 2,983,606. Other image dye-providing materials which may be used include, for example, initially diffusible coupling dyes such as are useful in the diffusion transfer process described in U.S. Pat. No. 3,087,817 which are rendered nondiffusible by coupling with the oxidation product of a color developer; initially nondiffusible dyes which release a diffusible dye following oxidation, sometimes referred to as "redox dye releaser" dyes, described in U.S. Pat. Nos. 3,725,062 and 4,076,529; initially nondiffusible image dye-providing materials which release a diffusible dye following oxidation and intramolecular ring closure as are described in U.S. Pat. No. 3,433,939 or those which undergo silver assisted cleavage to release a diffusible dye in accordance with the disclosure of U.S. Pat. No. 3,719,489; and initially nondiffusible image dye-providing materials which release a diffusible dye following coupling with an oxidized color developer as described in U.S. Pat. No. 3,227,550. The effect obtained upon any individual image dye-providing material will be dependent, at least in part, upon the distance between the compound and the image dye-providing material in the film unit.

The compounds may be incorporated into the photographic elements by any suitable technique. The compounds can be incorporated in the photographic element typically by being coated from a water or oil dispersion and the layer(s) in which they reside typically include a binder material such as gelatin or the like.

In a preferred embodiment of the invention, the compounds are utilized in diffusion transfer photographic film units in conjunction with initially diffusible dye developers as the image dye-providing materials. As described in U.S. Pat. No. 2,983,606 a photosensitive element containing a dye developer and a silver halide emulsion is photoexposed and a processing composition applied thereto, for example, by immersion, coating, spraying, flowing, etc., in the dark. The exposed photosensitive element is superposed prior to, during, or after the processing composition is applied, on a sheet-like support element which may be utilized as an image-receiving element. In a preferred embodiment, the processing composition is applied to the exposed photosensitive element in a substantially uniform layer as the photosensitive element is brought into superposed relationship with the image-receiving layer. The processing composition, positioned intermediate the photosensitive element and the image-receiving layer, permeates the emulsion to initiate development. The dye developer is immobilized or precipitated in exposed areas as a consequence of the development. In unexposed and partially exposed areas of the emulsion, the dye developer is unreacted and diffusible and thus provides an imagewise distribution of unoxidized dye developer, diffusible in the processing composition, as a function of the point-to-point degree of exposure of the silver halide emulsion. At least part of this imagewise distribution of unoxidized dye developer is transferred, by imbibition, to a superposed image-receiving layer or element, said transfer substantially excluding oxidized dye developer. The image-receiving layer receives a depthwise diffusion, from the developed emulsion, of unoxidized dye developer without appreciably disturbing the imagewise distribution thereof to provide a reversed or positive color image of the developed image. The image-receiving element may contain agents adapted to mordant or otherwise fix the diffused, unoxidized dye developer. In a preferred embodiment of said U.S. Pat. No. 2,983,606 and in certain commercial applications thereof, the desired positive image is revealed by separating the image-receiving layer from the photosensitive element at the end of a suitable imbibition period. Alternatively, as also disclosed in said U.S. Pat. No. 2,983,606, the image-receiving layer need not be separated from its superposed contact with the photosensitive element, subsequent to transfer image formation, if the support for the image-receiving layer, as well as any other layers intermediate said support and image-receiving layer, is transparent and a processing composition containing a substance, e.g., a white pigment, effective to mask the developed silver halide emulsion or emulsions is applied between the image-receiving layer and said halide emulsion or emulsions.

Dye developers, as noted in said U.S. Pat. No. 2,983,606, are compounds which contain, in the same molecule, both the chromophoric system of a dye and also a silver halide developing function. By "a silver halide developing function" is meant a grouping adapted to develop exposed silver halide. A preferred silver halide development function is a hydroquinonyl group. In general, the development function includes a benzenoid developing function, that is, an aromatic developing group which forms quinonoid or quinone substances when oxidized.

Multicolor images may be obtained using dye developers in diffusion transfer processes by several techniques. One such technique contemplates obtaining multicolor transfer image utilizing dye developers by employment of an integral multilayer photosensitive element, such as is disclosed in the aforementioned U.S. Pat. No. 2,983,606 and in U.S. Pat. No. 3,345,163, wherein at least two selectively sensitized photosensitive strata, superposed on a single support, are processed, simultaneously and without separation, with a single common image-receiving layer. A suitable arrangement of this type comprises a support carrying a red-sensitive silver halide emulsion stratum, a green-sensitive silver halide emulsion stratum and a blue-sensitive silver halide emulsion stratum, said emulsions having associated therewith, respectively, for example, a cyan dye developer, a magenta dye developer and a yellow dye developer. The dye developer may be utilized in the silver halide emulsion stratum, for example, in the form of particles, or it may be disposed in a stratum behind the appropriate silver halide emulsion strata. Each set of silver halide emulsion and associated dye developer strata may be separated from other sets by suitable interlayers, for example, by a layer or stratum of gelatin or polyvinyl alcohol. In certain instances, it may be desirable to incorporate a yellow filter in front of the green-sensitive emulsion and such yellow filter may be incorporated in an interlayer. However, where desirable, a yellow dye developer of the appropriate spectral characteristics and present in a state capable of functioning as a yellow filter may be so employed and a separate yellow filter omitted.

Particularly useful products for obtaining multicolor dye developer images are disclosed in U.S. Pat. No. 3,415,644. This patent discloses photographic products wherein a photosensitive element and an image-receiving are maintained in fixed relationship prior to exposure, and this relationship is maintained as a laminate after processing and image formation. In these products, the final image is viewed through a transparent (support) element against a light-reflecting, i.e., white background. Photoexposure is made through said transparent element and application of the processing composition provides a layer of light-reflecting material to provide a white background. The light-reflecting material (referred to in said patent as an "opacifying agent") is preferably titanium dioxide, and it also performs an opacifying function, i.e., it is effective to mask the developed silver halide emulsions so that the transfer image may be viewed without interference therefrom, and it also acts to protect the photo-exposed silver halide emulsions from post-exposure fogging by light passing through said transparent layer if the photoexposed film unit is removed from the camera before image formation is completed.

U.S. Pat. No. 3,647,437 is concerned with improvements in products and processes disclosed in said U.S. Pat. No. 3,415,644, and discloses the provision of light-absorbing materials to permit such processes to be preformed, outside of the camera in which photoexposure is effected, under much more intense ambient light conditions. A light-absorbing material or reagent, preferably a pH-sensitive phthalein dye, is provided so positioned and/or constituted as not to interfere with photoexposure but so positioned between the photoexposed silver halide emulsions and the transparent support during processing after photoexposure as to absorb light which otherwise might fog the photoexposed emulsions. Furthermore, the light-absorbing material is so positioned and/or constituted after processing as not to interfere with viewing the desired image shortly after said image has been formed. In the preferred embodiments, the light-absorbing material, also sometimes referred to as an optical filter agent, is initially contained in the processing composition together with a light-reflecting material, e.g., titanium dioxide. The concentration of the light-absorbing dye is selected to provide the light transmission opacity required to perform the particular process under the selected light conditions.

In a particularly useful embodiment, the light-absorbing dye is highly colored at the pH of the processing composition, e.g., 13-14, but is substantially non-absorbing of visible light at a lower pH, e.g., less than 10-12. This pH reduction may be effected by an acid-reacting reagent appropriately positioned in the film unit, e.g., in a layer between the transparent support and the image-receiving layer.

The dye developers are preferably selected for their ability to provide colors that are useful in carrying out subtractive color photography, that is, the previously mentioned cyan, magenta and yellow. The dye developers employed may be incorporated in the respective silver halide emulsion or, in the preferred embodiment, in a separate layer behind the respective silver halide emulsion, and such a layer of dye developer may be applied by use of a coating solution containing the respective dye developer distributed, in a concentration calculated to give the desired coverage of dye developer per unit area, in a film-forming natural, or synthetic, polymer, for example, gelatin, polyvinyl alcohol, and the like, adapted to be permeated by the processing composition.

Other diffusion transfer products and processes in which the dye developers of the present invention may be utilized are described in U.S. Pat. Nos. 3,573,043 and 3,594,165. For convenience, the entire disclosure of each of the six patents referred to immediately above is hereby incorporated by reference herein.

A particularly useful film unit according to the invention is one wherein the photosensitive element includes a light-reflecting layer between the silver halide layer and the image dye-providing material layer (as described in Canadian Pat. No. 668,592), the substrate of the photosensitive element carries the polymeric acid neutralizing layer which in turn carries the timing layer (as described in U.S. Pat. No. 3,573,043) and the processing composition includes an oximated polydiacetone acrylamide thickening agent (as described in U.S. Pat. No. 4,202,694).

In a preferred diffusion transfer film unit according to the invention which includes a compound within Formulas A, B and C wherein PHOTO is a development restrainer moiety within Formulas D-G, the compound is incorporated in the photosensitive element in a layer between the support of the element and the silver halide emulsion closest to that support. This structure combines a delay in the cleavage of the compound with a delay in the diffusion of the released development restrainer through the film unit. In another preferred embodiment of a diffusion transfer film unit a development restrainer precursor according to the invention is incorporated in the photosensitive element and the film unit is processed with a processing composition which includes 4-hydroxy phenylmercaptotetrazole.

In the Figure there is shown another preferred diffusion transfer film unit of the invention wherein the film unit 10 comprises a transparent support 14 carrying on a first side thereof a layer 12 of a transparent polymeric material adapted to convert to an opaque condition when contacted by an aqueous alkaline processing composition. On the opposed side of support layer 14 is shown a polymeric acid-reacting layer 16, timing layer 18, a blue sensitive silver halide emulsion layer 20, a yellow dye developer layer 22, an interlayer 24, a green sensitive silver halide emulsion layer 26, a magenta dye developer layer 28, and interlayer 30, a red sensitive silver halide emulsion layer 32, a cyan dye developer layer 34, an interlayer 36, an opaque/reflective layer 38 (which preferably contains a white pigment such as titanium dioxide to provide a white background against which the image is viewed and an opacification agent such as carbon black), an image receiving layer 40 and an anti-abrasion layer 42.

Photoexposure of the silver halide emulsion layers is effected through the transparent polymeric layer 12 and through transparent support 14 and the layer carried thereon, i.e., the polymeric acid layer 16 and the spacer or timing layer 18, which layers are also transparent, the film unit being so positioned within the camera that light admitted through the camera exposure or lens system is incident upon the outer or exposure surface 12a of the polymeric layer 12.

After photoexposure, the film unit is developed such as by immersing it in an aqueous alkaline processing composition. After a suitable imbibition period, e.g., in the range of about 40 to 120 seconds, the transparent polymeric layer 12 is converted by the alkaline processing composition to a highly colored, or opaque, layer. In addition, development of emulsion layers 20, 26 and 32 is initiated by contact with the processing composition. If the film unit is removed from the processing composition to conditions of ambient light, the still photosensitive and developing emulsion layers thereof are protected against additional photoexposure by ambient of environmental light through transparent support 14 by the now opaque layer 12. The emulsion layers are protected against additional photo-exposure from the opposed, or image-viewing, side of the film unit by opaque reflective layer 38.

In exposed and developed areas, the dye developers are oxidized as a function of the silver halide development and are immobilized. Unoxidized dye developer associated with undeveloped and partially developed areas remain mobile and is transferred to the image receiving layer 40 to provide the desired positive image therein.

Permeation of the alkaline processing composition through the several layers of the film unit is controlled so that the process pH is maintained at a high enough level to effect the requisite development and image transfer and to convert polymeric layer 12 to a highly colored form after which pH reduction is effected as a result of alkali permeation into the polymeric acid layer 16 such that the pH is reduced to a level which stops further dye transfer. Layer 12, after having been rendered opaque by the action of alkali, remains opaque notwithstanding this pH reduction. The image present in image receiving layer 40 is viewed through the anti-abrasion layer 42 against the reflecting layer 38 which provides an essential white background for the dye image and also effectively masks from view the developed silver halide emulsion layers and dye developer immobilized therein or remaining in the dye developer layers.

In the embodiment illustrated in the Figure image receiving layer 40 and reflecting layer 38 against which the image is viewed are shown as layers of the film unit 10. While this is a particularly useful and preferred embodiment, image formation can be accomplished in a separate image receiving element comprising a transparent or opaque (e.g., baryta) support and an image receiving layer. The image receiving element may be brought into superposed relation with a photosensitive element comprising layers 12 through 38, either before or after photoexposure thereof. Polymeric layer 12 can be rendered opaque and development can be initiated by contact with an aqueous alkaline processing composition. The image receiving element can be left intact for viewing through the transparent support thereof, a reflection print against reflective layer 38. Alternatively, the image receiving element can be separated for a viewing of a transparency or reflection print, respectively in the case of a transparent or opaque image receiving element support.

According to another embodiment, transparent polymeric layer 12 can, if desired, be positioned between transparent support 14 and polymeric acid layer 16. It will be appreciated, however, that owing to the amount of time required for alkali to permeate the several layers of the film unit so as to permit conversion of the transparent layer 12 to an opaque layer, the positioning shown in the Figure is preferred.

A quaternary nitrogen-containing polymer suitable for use in layer 12 is disclosed and claimed in copending, commonly assigned application Ser. No. 492,696 filed on even date herewith.

It should be noted here that other opacification systems may be used in layer 12. Further, it should also be recognized that photoexposure and processing of the film unit can be carried out in the dark in which case layer 12 is not required.

The use of sodium cellulose sulfate in the anti-abrasion layer 42 is disclosed and claimed in copending, commonly assigned application Ser. No. 492,731 filed on even date herewith.

The invention will now be described further in detail with respect to specific preferred embodiments by way of examples, it being understood that these are illustrative only and the invention is not intended to be limited to the materials, conditions, process parameters, etc., which are recited therein.

EXAMPLE I

To thionyl chloride (170 ml, 2.35 m) stirred at room temperature there was added portion-wise over a ten minute period with exclusion of moisture, 64 g (0.48 m) of 4-hydroxymethylimidazole hydrochloride. With each addition vigorous evolution of gas occurred and occasional cooling by ice/water bath was necessary to keep the temperature below 30° C. The resulting greenish solution was stirred at 30° C. for an additional ten minutes until the gas evolution subsided. The temperature was then raised to 55°±5° C. for forty minutes during which time a thick gelatinous precipitate formed. The reaction mixture was cooled and excess thionyl chloride removed under reduced pressure at 30° C. The yellow residue was triturated with 100 ml of ether, collected and washed four times with 50 ml of ether. The product, a very pale yellow powder, was dried in a stream of air to give 70.88 g (96.5% yield) of 4-chloromethylimidazole hydrochloride m.p. 145°–6° C. which was stored under refrigeration.

$C_4H_6N_2Cl_2$ requires 31.40%C, 3.95%H, 18.31%N and 46.34%Cl. Elemental analysis found 31.30%C, 4.01%H, 18.34%N and 47.17%Cl.

N,N-di-isopropylethylamine (77.6 g, 0.6 m) was added in a slow stream at room temperature to a stirred solution of phenylmercaptotetrazole (53.4 g, 0.3 m) in 250 ml of dimethylformamide under nitrogen in an ice/water bath to keep the temperature below 30° C. To the resulting orange solution there was added rapidly 4-chloromethylimidazole hydrochloride (45.9 g, 0.3 m) while keeping the temperature between 30° and 40° C. After ten minutes the resulting orange solution was cooled and poured slowly into 1500 ml of rapidly stirred ice/water mixture. The resulting colorless precipitate was collected and washed several times with cold water. The solid was dried in a stream of air to give 70.35 g (91% yield) of Compound I, a colorless powder, m.p. 136°–7° C. (dec.).

The structure of the product was confirmed by IR, $^{13}C$ NMR and proton NMR spectra.

$C_{11}H_{10}N_6S$ requires 51.15%C, 3.90%H, 32.54%N and 12.41%S. Elemental analysis found 51.16%C, 3.95%H, 32.56%N and 12.51%S.

EXAMPLE II

Thionyl chloride (50 ml) was stirred under nitrogen in an ice bath while 4-hydroxymethyl-5-methylimidazole (11.2 g, 0.1 m) was added in very small portions over a 15 minute period. The reaction was vigorous and the temperature was maintained between 10° and 20° C. A colorless precipitate formed. When the addition was complete, the temperature was raised slowly (about ½ hour) to 55°±5° C. and maintained at that level for about ½ hour. The mixture was then cooled to 10° C. and diluted with 100 ml of diethyl ether. The colorless precipitate was collected by filtration, washed well with diethyl ether and dried in air to give 15.23 g (91% yield) of 4-methyl-5-chloromethyl imidazole hydrochloride, m.p. 208°–211° C. (dec.).

$C_5H_7N_2Cl$ HCl requires 35.95%C, 4.83%H, 16.77%N and 42.45%Cl. Elemental analysis found 33.67%C, 4.60%H, 15.70%N and 39.73%Cl.

A solution of phenylmercaptotetrazole (5.87 g, 0.033 m) in 50 ml of dimethylformamide was stirred at 20° C. under dry nitrogen. N,N-di-isopropylethylamine (8.53 g, 0.066 m) was added slowly over a five minute period while maintaining the temperature between 15°–20° C. with an ice/water bath. To the resulting orange solution there was added, portionwise over a five minute period at 15°–20° C., 4-chloromethyl-5-methylimidazole hydrochloride (5.51 g, 0.033 m). A slightly cloudy yellow solution formed. The solution was stirred at room temperature for 10 minutes and then poured into 300 ml of rapidly stirred ice/water. The resulting colorless precipitate was collected by filtration, washed with water and dried in air to give 6.32 g (70% yield) of Compound II, a colorless powder, m.p. 140°–142° C. (dec.).

$C_{12}H_{12}N_6S$ requires 52.93%C, 4.44%H, 30.86%N and 11.77%S. Elemental analysis found 52.79%C, 4.55%H, 30.79%N and 11.73%S.

The structure of the product was confirmed by IR and $^{13}C$ NMR spectra.

EXAMPLE III

To a solution of 2.35 g (0.01 m) of 1-[4-(hydroxyiminoethyl)phenyl]-1H-tetrazole-5-thiol in 10 ml of dimethylformamide there were added 2.5 g (0.02 m) of N,N-di-isopropylethylamine and the solution chilled in an ice/salt bath. To this solution there was added, all at once, a solution of 4-chloromethylimidazole hydrochloride (1.53 g, 0.01 m) in 5 ml of dimethylformamide. After stirring at 0°–5° C. for 15 minutes under nitrogen, the dark solution was poured into 300 ml of rapidly stirred ice water. The resulting yellow solid was filtered, washed with water and air dried to give 2.96 g (91% yield) of Compound III, a yellow solid, m.p. 170.5°–172.5° C. (dec.).

$C_{13}H_{13}N_7OS.\frac{1}{2}H_2O$ requires 48.27%C, 4.30%H, 30.22%N, 10.05%S and 7.32%O. After drying the product for four hours at 50° C. under reduced pressure, elemental analysis found 48.22%C, 4.38%H, 30.05%N, 7.41%O and 10.01%S.

The structure of the product was confirmed by IR and $^{13}C$ NMR spectra.

EXAMPLE IV

A mixture of 4-chloromethylimidazole hydrochloride (2.60 g, 0.017 m) and N,N'-dimethylthiourea (1.77 g, 0.017 m) in 25 ml of dimethylformamide was heated at 100° C. under nitrogen with stirring for 15 minutes. The mixture was cooled and poured into 100 ml of acetone. The resulting precipitate was collected, washed well with acetone and dried in air to give 3.54 g (81% yield) of Compound IV, a colorless powder, m.p. (dec.) 214°–215° C.

The structure of the product was confirmed by $^{13}C$ NMR and IR spectra.

$C_7H_{12}N_4S.2HCl$ requires 32.68%C, 5.45%H, 21.79%N, 12.45%S and 27.63%Cl. Elemental analysis found 32.64%C, 5.58%H, 21.72%N, 12.46%S and 27.49%Cl.

EXAMPLE V 4-chloromethylimidazole hydrochloride (3.06 g, 0.020 m) was added to a solution of thiourea (1.52 g, 0.020 m) in 25 ml of dimethylformamide and the resulting yellow solution was stirred under nitrogen at 100° C. for 15 minutes during which time a colorless solid separated from solution. The mixture was cooled in an ice bath and the precipitate was collected, washed with cold dimethylformamide and then ethyl ether and then dried in air to give 4.29 g (94% yield) of Compound V, a colorless powder, m.p. (dec.) 230°–232° C.

The structure of the product was confirmed by $^{13}C$ NMR and IR spectra.

$C_5H_8N_4S.2HCl$ requires 26.21%C, 4.40%H, 24.45%N, 13.99%S and 30.95%Cl. Elemental analysis found 26.38%C, 4.43%H, 24.49%N, 13.84%S and 31.11%Cl.

EXAMPLE VI

Trimethylthiourea (2.48 g) was stirred in 20 ml of dimethylformamide at room temperature. A small amount of insoluble material (0.20 g) was filtered off and 4-chloromethylimidazole hydrochloride ((2.95 g, 0.019 m) was added to the solution and stirred at 100° C. under nitrogen for 20 minutes. The resulting clear solution was allowed to stand overnight and then poured into 150 ml of chilled ethyl ether containing 25 ml of 2-propyl alcohol. A gummy material separated out. The liquors were decanted, replaced with fresh solvent and decanted again. The residue was treated with 100 ml of acetone and refrigerated overnight when solidification occurred. The solid was crushed, collected by filtration, washed well with acetone and dried in air to give 3.85 g (75% yield) of Compound VI, a colorless powder, m.p. (dec.) 156°–158° C.

The structure was confirmed with $^{13}C$ NMR and IR spectra.

$C_8H_{14}N_4S.2HCl$ requires 35.43%C, 5.95%H, 20.66%N, 11.82%S and 26.14%Cl. Elemental analysis found 34.69%C, 6.01%H, 20.22%N, 11.49%S and 27.76%Cl.

EXAMPLE VII 4-chloromethylimidazole hydrochloride (3.97 g, 0.0259 m) was added to a solution of 4-methylthiosemicarbazide (2.73 g, 0.0259 m) in 25 ml of dimethylformamide at 80° C. and the resulting pale yellow solution was stirred at 80° C. for 10 minutes during which time a thick precipitate separated out. The mixture was cooled, filtered and the solid washed sparingly with dimethylformamide and then ethyl ether, and then dried in a stream of air to give 5.51 g (82% yield) of Compound VII, a colorless powder m.p. (dec.) 196°–197° C.

The structure of the product was confirmed by $^{13}C$ NMR and IR spectra.

$C_6H_{11}N_5S.2HCl$ requires 27.91%C, 5.08%H, 27.13%N, 12.42%S and 27.46%Cl. Elemental analysis found 28.14%C, 5.26%H, 27.03%N, 12.33%S and 27.31%Cl.

EXAMPLE VIII 4-chloromethyl-5-methylimidazole hydrochloride (2.51 g, 0.015 m) was added to a solution of N,N'-dimethylthiourea (1.56 g, 0.015 m) in 25 ml of dimethylformamide and the mixture stirred under nitrogen for 20 minutes at 100° C. The resulting pale yellow solution was cooled and filtered into 150 ml of stirred ice-cold acetone. A gummy solid separated out. The liquors were decanted, replaced and decanted again. The residue was treated with 25 ml of 2-propyl alcohol at 0° C. and refrigerated overnight. The resulting crystalline solid was crushed, filtered off, washed sparingly with cold 2-propyl alcohol and then ethyl ether and dried in air to give 2.14 g (53% yield) of compound VIII, a colorless powder, m.p. (dec.) 180°–182° C.

The structure of the product was confirmed by $^{13}C$ NMR and IR spectra.

$C_8H_{14}N_4S.2HCl$ requires 35.43%C, 5.95%H, 20.66%N, 11.82%S and 26.14%Cl. Elemental analysis found 35.32%C, 5.97%H, 20.43%N, 11.74%S and 25.94%Cl.

EXAMPLE IX

Compound IX was prepared in the same manner described in EXAMPLE VIII with the exception that thiourea (1.14 g, 0.015 m) was used in place of N,N'-dimethylthiourea. The procedure gave 2.81 g (77% yield) of Compound IX, a colorless powder, m.p. (dec.) 191°–192° C.

The structure of the product was confirmed by $^{13}C$ NMR and IR spectra.

$C_6H_{10}N_4S.2HCl$ requires 29.64%C, 4.97%H, 23.04%N, 13.19%S and 29.16%Cl. Elemental analysis found 30.55%C, 5.23%H, 22.57%N, 12.78%S and 27.68%Cl.

EXAMPLE X

4-Chloromethyl-5-methylimidazole hydrochloride (3.06 g, 0.020 m) was added to a solution of N,N'-diethylthiourea (2.64 g, 0.020 m) in 25 ml of dimethylformamide at 100° C. under nitrogen and the mixture stirred for 20 minutes. The solution was then cooled in an ice bath and the colorless solid which separated was collected, washed sparingly with dimethylformamide and ethyl ether and dried in air to give 4.26 g (75% yield) of Compound X, a colorless solid, m.p. (dec.) 195°–196° C.

The structure of the product was confirmed by $^{13}C$ NMR and IR spectra.

$C_9H_{16}N_4S.2HCl$ requires 37.90%C, 6.36% H, 19.64%N, 11.24%S and 24.86%Cl. Elemental analysis found 38.03%C, 6.36%H, 19.53%N, 11.06%S and 25.03%Cl.

EXAMPLE XI

2-Chloromethylimidazole hydrochloride (1.53 g, 0.010 m) was added to a solution of N,N'-dimethylthiourea (1.04 g, 0.010 m) in 20 ml of dimethylformamide at 60° C. and the mixture stirred under nitrogen for 15 minutes. The mixture was cooled in an ice/salt/water bath and the solid collected, washed it with acetone and dried in air to give 2.01 g (78% yield) of Compound XI, a pale yellow crystalline solid, m.p. (dec.) 225° C.

The structure of te product was confirmed by $^{13}C$ NMR and IR spectra.

$C_7H_{12}N_4S.2HCl$ requires 32.9%C, 5.49%H, 21.78%N, 12.47%S and 27.57%Cl. Elemental analysis found 32.55%C, 5.60%H, 21.69%N, 12.27%S and 27.74%Cl.

EXAMPLE XII

Compound XII was prepared by the procedure described in Example XI with the exception that thiourea (0.76 g, 0.010 m) was used in place of N,N'-dimethylthiourea. The procedure gave 1.61 g (70% yield) of Compound XII, a pale yellow powder, m.p. (dec.) 227°–228° C.

The structure of the product was confirmed by $^{13}C$ NMR and IR spectra.

$C_5H_8N_4S.2HCl$ requires 26.21%C, 4.40%H, 24.45%N, 13.99%S and 30.95%Cl. Elemental analysis found 26.41%C, 4.50%H, 24.27%N, 13.92%S and 30.77%Cl.

EXAMPLE XIII

4-Chloromethylimidazole hydrochloride (3.06 g, 0.20 m) was added to a solution of N,N'-diallylthiourea (3.12 g, 0.020 m) in 20 ml of dimethylformamide and the mixture stirred under nitrogen at 100° C. for 20 minutes. The solution was then cooled. Upon standing overnight, yellow crystals separated from the yellow solution. The mixture was diluted with 50 ml of 2-propyl alcohol and the crystals crushed and collected by filtration. The solid was washed sparingly with 2-propyl alcohol and then with ethyl ether and dried in air to give 4.24 g (69% yield) of Compound XIII, a colorless powder, m.p. (dec.) 164°–165° C.

The structure was confirmed by $^{13}C$ NMR and IR spectra.

$C_{11}H_{16}N_4S.2HCl$ requires 42.72%C, 5.87%H, 18.12%N, 10.37%S and 22.93%Cl. Elemental analysis found 42.59%C, 5.81%H, 18.10%N, 10.45%S and 23.15%Cl.

EXAMPLE XIV

As a control, a film unit was prepared as follows: the negative element comprised an opaque subcoated polyethylene terephthalate film base on which the following layers were coated in succession:

1. as a polymeric acid layer approximately 9 parts of a ½ butyl ester of polyethylene/maleic anhydride copolymer and 1 part of polyvinyl butyral coated at a coverage of about 26,460 mgs./m.$^2$;

2. a timing layer comprising about 97% of a 60-29-6-4-0.4 pentapolymer of butylacrylate, diacetone acrylamide, methacrylic acid, styrene and acrylic acid and about 3% polyvinylalcohol coated at a coverage of about 3000 mgs./m.$^2$;

3. a cyan dye developer layer comprising about 511 mgs./m.$^2$ of a cyan developer represented by the formula

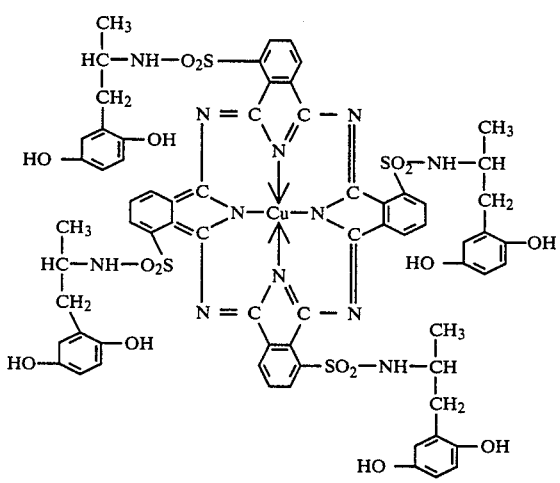

about 70 mgs./m.$^2$ of 4'-methyl phenyl hydroquinone and about 317 mgs./m.$^2$ of gelatin;

4. a red-sensitive silver iodobromide emulsion layer comprising about 1378 mgs./m.$^2$ of silver and about 827 mgs./m.$^2$ of gelatin;

5. an interlayer comprising about 2090 mgs./m.$^2$ of the pentapolymer described in layer 2, about 110 mgs./m.$^2$ of polyacrylamide and about 44 mgs./m.$^2$ of succinaldehyde;

6. a magenta dye developer layer comprising about 460 mgs./m.$^2$ of a magenta dye developer represented by the formula

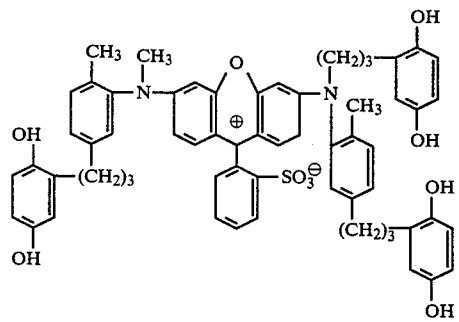

and about 210 mgs./m.$^2$ of gelatin;

7. a green-sensitive silver iodobromide emulsion layer comprising abou 723 mgs./m.$^2$ of silver and about 318 mgs./m.$^2$ of gelatin;

8. an interlayer comprising about 1881 mgs./m.$^2$ of the pentapolymer described in layer 2 and about 99 mgs./m.$^2$ of polyacrylamide;

9. a yellow dye developer layer comprising about 689 mgs./m.² of a yellow dye developer represented by the formula

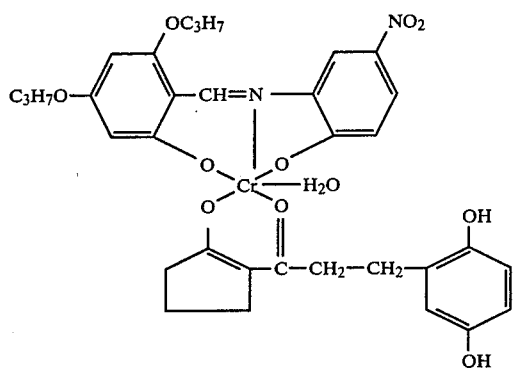

and about 265 mgs./m.² of gelatin;

10. a blue-sensitive silver iodobromide emulsion layer comprising about 764 mgs./m.² of silver, about 499 mgs./m.² of gelatin and about 265 mgs./m.² of 4-methyl phenyl hydroquinone;

11. a gelatin layer coated at a coverage of about 400 mgs./m.²; and 12. a topcoat layer coated at a coverage of about 20 mgs./ft.² (215 mgs./m.²) of gelatin.

The image-receiving element comprised a transparent subcoated polyethylene terephthalate film base upon which there was coated an image-receiving layer coated at a coverage of about 300 mgs./ft.² (3229 mgs./m.²) of a graft copolymer comprised of 4-vinylpyridine (4VP) and vinyl benzyl trimethyl ammonium chloride (TMQ) grafted onto hydroxyethyl cellulose (HEC) at a ratio HEC/4VP/TMQ of 2.2/2.2/1; and about 5 mgs./ft.² (53.8 mgs./m.²) of 1,4-butanediol diglycidyl ether.

The film unit was processed with a processing composition made up as follows

| | Weight Percent |
|---|---|
| Titanium dioxide | 47.9 |
| Oximated polydiacetone acrylamide | 0.66 |
| Potassium hydroxide | 4.36 |
| Benzothiazole | 0.45 |
| Hypoxanthine | 0.10 |
| 6-methyl uracil | 0.25 |
| 6-bromo-5-methyl-4-azabenzimidazole | 0.10 |
| Colloidal silica | 0.54 |
| N—phenethyl-α-picolinium bromide | 1.06 |
| Polyethylene glycol (MW 4000) | 0.37 |
| 3,5-dimethyl pyrazole | 0.16 |
| 2-methylimidazole | 0.69 |
| Phenylmercaptotetrazole | 0.04 |
| Nickel acetate | 0.4 |
| N—hydroxyethyl-N,N',N'—triscarboxymethyl ethylene diamine | 0.62 |

-continued

| | Weight Percent |
|---|---|
| ![structure] HOOC, H N, H N, NH—SO₂—C₁₆H₃₃—n, O, O | 0.29 |
| ![structure] C₁₈H₃₇O, OH, COOH, HOOC, OH, O, O | 1.38 |
| Water to make 100% | |

The negative element was exposed (2 meter-candle-seconds) on a sensitometer to a test scale with white light and then brought together with the image-receiving element and processed at 75° F. by passing the film unit through a pair of rollers set at a gap spacing of about 0.0028 inch. The film unit was kept intact and viewed through the base of the image-receiving element.

Identical film units were processed in the same manner at 45° F. and 95° F., respectively. The neutral density columns of the images were read on a densitometer to obtain the Dmax and Dmin values for red, green and blue, respectively.

A film unit according to the invention was prepared. This was identical to the Control with the exception that the negative further included about 20 mgs./ft.² (215 mgs./m.²) of Compound III in the topcoat layer. The film unit was processed as described above at 45° F., 75° F. and 95° F.

TABLE II

| FILM | Dmax | | | Dmin | | |
|---|---|---|---|---|---|---|
| UNIT | R | G | B | R | G | B |
| | 45° F. | | | | | |
| Control | 1.48 | 1.79 | 1.92 | 0.17 | 0.15 | 0.19 |
| A | 1.49 | 1.89 | 1.93 | 0.19 | 0.18 | 0.19 |
| | 75° F. | | | | | |
| Control | 1.59 | 1.50 | 1.38 | 0.16 | 0.14 | 0.16 |
| A | 1.79 | 1.98 | 1.65 | 0.19 | 0.18 | 0.19 |
| | 95° F. | | | | | |
| Control | 1.38 | 1.21 | 1.12 | 0.16 | 0.14 | 0.17 |
| A | 1.35 | 1.25 | 1.15 | 0.19 | 0.20 | 0.21 |

It can be seen that Film Unit A had significantly higher red, green and blue Dmax at 75° F. and slightly higher green and blue Dmax at 95° F.

EXAMPLE XV

As a control, a film unit was prepared wherein a transparent subcoated polyethylene terephthalate photographic film base had coated on it the following layers in succession:

1. a polymeric acid layer coated at a coverage of about 10,000 mgs./m.$^2$ and made up of approximately 9 parts of ½ butyl ester of polyethylene/maleic anhydride copolymer and 1 part of polyvinyl butyral;
2. a timing layer coated at a coverage of about 2500 mgs./m.$^2$ of a 39/39/1.5/0.5/20 pentapolymer of diacetone acrylamide, butyl acrylate, acrylic acid, 2-acrylamido-2-methylpropane sulfonic acid and 2-cyanoethyl acrylate;
3. a blue sensitive silver iodobromide emulsion layer coated at a coverage of about 1300 mgs./m.$^2$ of silver (1.11 microns) and about 650 mgs./m.$^2$ of gelatin;
4. A yellow dye developer layer made up of about 1150 mgs./m.$^2$ of the yellow dye developer illustrated in EXAMPLE XIV; about 566 mgs./m.$^2$ of gelatin and about 115 mgs./m.$^2$ of 4'-methyl phenyl hydroquinone;
5. as an interlayer, a matrix system comprising 70 parts of a 50.5/44/5/0.5 matrix copolymer of diacetone acrylamide/butyl acrylate/acrylic acid/2-acrylamido-2-methylpropane sulfonic acid and polymerized therein 30 parts of 72/28 copolymer of 2-cyanoethyl acrylate/diacetone acrylamide, the matrix system coated at a coverage of about 2000 mgs./m.$^2$ and about 17 mgs./m.$^2$ of succindialdehyde;
6. a green sensitive silver iodobromide emulsion layer coated at a coverage of about 896 mgs./m.$^2$ of silver (1.11 microns) and about 394 mgs./m.$^2$ of gelatin;
7. a magenta dye developer layer made up of about 500 mgs./m.$^2$ of the magenta dye developer illustrated in EXAMPLE XIV; about 321 mgs./m.$^2$ of gelatin and about 77 mgs./m.$^2$ of 4'-methyl phenyl hydroquinone;
8. an interlayer comprising the matrix system of layer 5 at a coverage of about 1500 mgs./m.$^2$ and about 13 mgs./m.$^2$ of succindialdehyde;
9. a red-sensitive silver iodobromide emulsion layer coated at a coverage of about 866 mgs./m.$^2$ of silver (1.11 microns) and about 520 mgs./m.$^2$ of gelatin;
10. a cyan dye developer layer made up of about 350 mgs./m.$^2$ of the cyan dye developer illustrated in EXAMPLE XIV, about 266 mgs./m.$^2$ of gelatin and about 100 mgs./m.$^2$ of 4'-methyl phenyl hydroquinone;
11. as an interlayer, a matrix system comprising 70 parts of a 49/42.5/8/0.5 matrix copolymer of diacetone acrylamide/butylacrylate/acrylic acid/2-acrylamido-2-methylpropane sulfonic acid and polymerized therein 30 parts of a 72/78 copolymer of 2-cyanoethyl acrylate/diacetone acrylamide, the matrix system coated at a coverage of about 2000 mgs./m.$^2$;
12. an opacification layer made up of about 1500 mgs./m.$^2$ of carbon black and about 422 mgs./m.$^2$ polyethylene oxide;
13. a reflective layer made up of about 11,000 mgs./m.$^2$ of titanium dioxide, about 1467 mgs./m.$^2$ of polyethylene oxide, about 917 mgs./m.$^2$ of Rhoplex HA-12 polyacrylamide latex (Rohm & Haas) and about 1467 mgs./m.$^2$ of polytetrafluoroethylene (duPont Teflon 30);
14. an image-receiving layer coated at a coverage of about 2000 mgs./m.$^2$ of a graft copolymer comprised of 4-vinyl pyridine (4VP) and vinyl benzyl trimethylammonium chloride (TMQ) grafted onto hydroxyethyl cellulose (HEC) at a ratio HEC/4VP/TMQ of 2.2/2.2/1; and
15. a topcoat layer made up of about 4000 mgs./m.$^2$ of sodium cellulose sulfate and about 58 mgs./m.$^2$ of polyacrylamide.

The film unit was exposed (2 meter-candle-seconds) to a test target, or step wedge, through the transparent base and then processed, in the dark, by immersing it for two minutes in a processing composition made up of:

|  | Parts By Weight |
| --- | --- |
| Potassium hydroxide | 5.0 |
| N—(n-pentyl)-α-picolinium bromide | 2.2 |
| Tetramethyl reductic acid | 0.2 |
| Zinc acetate | 0.74 |
| Water to make 100% | |

The film unit was then removed from the processing composition, passed through a pair of rubber rollers at a zero gap and allowed to remain in the dark for four minutes.

A washed out image was obtained. The red, green and blue Dmax and Dmin values in the neutral density column were read on a densitometer. In addition, the speeds of the red, green and blue curves, obtained at the density resulting from an exposure of 0.125 meter-candle-second (fifth step of the neutral density column) were read. Meaningful results could not be obtained for the speeds because of the quality of the image.

In addition, Film Units A and B according to the invention were prepared. These film units were identical to the control with the following exceptions:

Film Unit A further included Compound I in the following amounts: about 45 mgs./m.$^2$ in layer 4; about 30.5 mgs./m.$^2$ in layer 7; and about 30.5 mgs./m.$^2$ in layer 10.

Film Unit B further included Compound II in the following amounts: about 47 mgs./m.$^2$ in layer 4; about 32 mgs./m.$^2$ in layer 7; and about 32 mgs./m.$^2$ in layer 10.

The Film Units according to the invention were processed as described above at 15° C., 22° C. (room temperature), 26° C. and 30° C. Excellent images with superior color saturation in the color columns were obtained. The Dmax, Dmin and speed values for red, green and blue are shown in Table III.

TABLE III

| FILM UNIT | | R | G | B | SPEED R | G | B |
| --- | --- | --- | --- | --- | --- | --- | --- |
| | | | | 22° C. | | | |
| Control | Dmax | 0.38 | 0.34 | 0.38 | — | — | — |
| | Dmin | 0.18 | 0.18 | 0.20 | | | |
| A | Dmax | 1.61 | 2.35 | 2.19 | 0.43 | 0.58 | 0.41 |
| | Dmin | 0.18 | 0.18 | 0.22 | | | |
| B | Dmax | 1.61 | 2.40 | 2.33 | 0.60 | 0.90 | 0.78 |
| | Dmin | 0.22 | 0.23 | 0.27 | | | |
| | | | | 15° C. | | | |
| A | Dmax | 1.72 | 2.31 | 2.18 | 0.51 | 0.58 | 0.47 |
| | Dmin | 0.19 | 0.19 | 0.23 | | | |
| B | Dmax | 1.67 | 2.40 | 2.36 | 0.75 | 0.94 | 0.82 |
| | Dmin | 0.23 | 0.24 | 0.28 | | | |
| | | | | 26° C. | | | |
| A | Dmax | 1.46 | 2.31 | 1.83 | 0.31 | 0.44 | 0.31 |
| | Dmin | 0.15 | 0.17 | 0.18 | | | |
| B | Dmax | 1.48 | 2.39 | 2.26 | 0.42 | 0.71 | 0.65 |
| | Dmin | 0.17 | 0.18 | 0.20 | | | |
| | | | | 30° C. | | | |
| A | Dmax | 1.29 | 2.09 | 1.20 | 0.30 | 0.45 | 0.29 |

TABLE III-continued

| FILM UNIT | | R | G | B | SPEED R | G | B |
|---|---|---|---|---|---|---|---|
| B | Dmin | 0.16 | 0.19 | 0.19 | | | |
|   | Dmax | 1.46 | 2.38 | 2.09 | 0.41 | 0.72 | 0.68 |
|   | Dmin | 0.17 | 0.19 | 0.21 | | | |

It can be seen that the restrainer release materials of the invention provide satisfactory sensitometry for the film units with respect to Dmax, Dim and photographic speed. Film Units A and B exhibited acceptable density levels over the processing temperature range exemplified. It is further evident that the film units of the invention exhibited good performance at elevated temperatures, i.e., above room temperature. In particular, Film Unit B exhibited good results at such elevated temperatures.

Although the invention has been described with respect to various preferred embodiments, it is not intended to be limited thereto but rather those skilled in the art will recognize that variations and modifications may be made therein which are within the spirit of the invention and the scope of the appended claims.

What is claimed is:

1. A photographic element comprising a support and at least one layer thereon containing a silver halide emulsion having associated therewith a compound represented by the formula $$\text{PHOTO}-\underset{R_5}{\overset{R_4}{\underset{|}{\overset{|}{C}}}}-\underset{N}{\overset{R_3}{\underset{|}{\overset{|}{\diagdown}}}}\text{N}-R_2$$
$$\phantom{xxxxxx}R_1$$

wherein $R_1$ is hydrogen, a hydrolyzable group or a group which is cleavable in aqueous alkaline environment;

$R_2$ and $R_3$ are the same or different and are hydrogen, a substituent which modifies a property of said compound, or, when $$-\underset{R_5}{\overset{R_4}{\underset{|}{\overset{|}{C}}}}-\text{PHOTO}$$

is attached to the 2-position, taken together form a five or six member carbocyclic or heterocyclic ring;

$R_4$ and $R_5$ are the same or different and are hydrogen or alkyl; and

PHOTO is a moiety represented by the formula $$-A-C=\!\!=\!\!N \text{ or } -N-C=\!\!=\!\!A$$
$$\phantom{xxx}\overset{|}{X}\phantom{xxxxxxx}\overset{|}{X}$$

wherein A is sulfur or selenium; and X represents the nonmetallic atoms necessary to form a nucleus which completes a five or six member heterocyclic moiety; or a photographically acceptable acid addition salt thereof.

2. A photographic element is defined in claim 1 wherein said silver halide emulsion has associated therewith an image dye-providing material.

3. A photographic element as defined in claim 2 wherein said image dye-providing material is a dye developer.

4. A photographic element as defined in claim 1 wherein X represents the nonmetallic atoms which complete a tetrazole ring.

5. A photographic element as defined in claim 4 wherein PHOTO is $$-A-\underset{\phantom{x}}{\overset{\phantom{x}}{\diagup}}\overset{N-\!\!\!-\!\!\!-\!\!\!-N}{\underset{N}{\diagdown\!\!\!\diagup}}\overset{\|}{\underset{|}{N}}$$
$$\phantom{xxxxx}\text{Ph}$$

6. A photographic element as defined in claim 5 wherein A is sulfur.

7. A photographic element as defined in claim 6 wherein $R_2$ or $R_3$ is alkyl.

8. A photographic element as defined in claim 4 wherein PHOTO is (structure with phenyl substituted with $R_{11}$)

wherein $R_{11}$ is either a group having a pKa of from about 7 to about 14 which is ionizable to an anion whereby the silver salt resulting from the cleavage of $$-\underset{R_5}{\overset{R_4}{\underset{|}{\overset{|}{C}}}}-\text{PHOTO}$$

is more soluble in the pH range within which $R_{11}$ is ionized to an anion than it is below that pH range, or a precursor thereof.

9. A photographic element as defined in claim 8 wherein A is sulfur.

10. A photographic element as defined in claim 8 wherein $R_{11}$ is selected from the group consisting of —OH, $$-\overset{O}{\underset{\|}{C}}-CH_3, \quad -O-\overset{O}{\underset{\|}{C}}-CH_3,$$

—SO$_2$NH$_2$, —SO$_2$NHCH$_3$, —SO$_2$NHC$_8$H$_{17}$, —NHSO$_2$CH$_3$, $$-\text{NHSO}_2-\!\!\!\diagup\!\!\!\!\!\diagdown-CH_3 \text{ and } -\overset{N-OH}{\underset{\|}{C}}-Z,$$

wherein Z is H, alkyl having from 1 to 10 carbon atoms, aralkyl, phenyl or substituted phenyl.

11. A photographic product for use in forming a multicolor diffusion transfer image comprising a photosensitive element comprising a support carrying a blue-sensitive silver halide emulsion having a yellow dye developer associated therewith, a green-sensitive silver halide emulsion having a magenta dye developer associated therewith and a red-sensitive silver halide emulsion having a cyan dye developer associated therewith, a second sheet-like element positioned in superposed or superposable relationship with said photosensitive element, an image receiving layer positioned in one of said elements, a rupturable container releasably holding an aqueous alkaline processing composition adapted, when distributed between a pair of predetermined layers carried by said photosensitive element and said second element, to develop said silver halide emulsions and provide a multicolor diffusion transfer image on said image-receiving layer, at least one of said photosensitive and said second elements including a compound represented by the formula

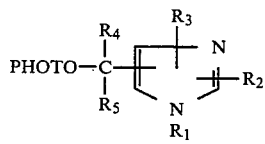

wherein
$R_1$ is hydrogen, a hydrolyzable group or a group which is cleavable in aqueous alkaline environment;
$R_2$ and $R_3$ are the same or different and are hydrogen, a substituent which modifies a property of said compound, or, when

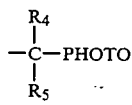

is attached to the 2-position, taken together form a five or six member carbocyclic or heterocyclic ring;
$R_4$ and $R_5$ are the same or different and are hydrogen or alkyl; and
PHOTO is a moiety represented by the formula

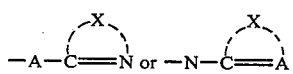

wherein A is sulfur or selenium; and X represents the nonmetallic atoms necessary to form a nucleus which completes a five or six member heterocyclic moiety; or a photographically acceptable acid addition salt thereof.

12. A product as defined in claim 11 wherein said second element includes said image receiving layer and said processing composition includes titanium dioxide.

13. A photographic product as defined in claim 11 wherein X represents the nonmetallic atoms which complete a tetrazole moiety.

14. A photographic product as defined in claim 13 wherein PHOTO is

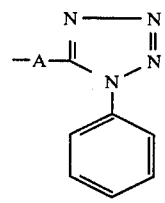

15. A photographic product as defined in claim 14 wherein A is sulfur.

16. A photographic product as defined in claim 13 wherein PHOTO is

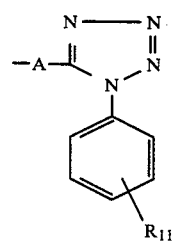

wherein $R_{11}$ is either a group having a pKa of from about 7 to about 14 which is ionizable to an anion whereby the silver salt resulting from the cleavage of

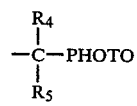

is more soluble in the pH range within which $R_{11}$ is ionized to an anion that it is below that pH range, or a precursor thereof.

17. A photographic product as defined in claim 16 wherein $R_{11}$ is selected from the group consisting of —OH,

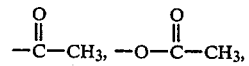

—SO$_2$NH$_2$, —SO$_2$NHCH$_3$, —SO$_2$NHC$_8$H$_{17}$, —NHSO$_2$CH$_3$,

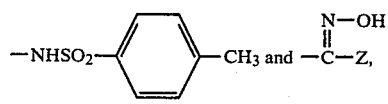

where Z is hydrogen, alkyl having from 1 to 10 carbon atoms, aralkyl, pheny or substituted phenyl.

18. A diffusion transfer photographic element comprising a transparent support carrying a photosensitive system comprising a silver halide emulsion layer in association with an image dye-providing material layer and an image receiving layer, said photosensitive system including a compound represented by the formula

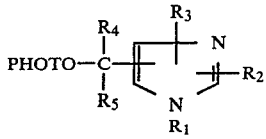

wherein $R_1$ is hydrogen, a hydrolyzable group or a group which is cleavable in aqueous alkaline environment;

$R_2$ and $R_3$ are the same or different and are hydrogen, a substituent which modifies a property of said compound, or, when

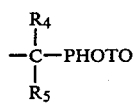

is attached to the 2-position, taken together form a five or six member carbocyclic or heterocyclic ring;

$R_4$ and $R_5$ are the same or different and are hydrogen or alkyl; and

PHOTO is a moiety represented by the formula

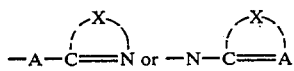

wherein A is sulfur or selenium; and X represents the nonmetallic atoms necessary to form a nucleus which completes a five or six member heterocyclic moiety; or a photographically acceptable acid addition salt thereof.

19. A photographic element as defined in claim 18 and further including an opacification layer comprising an initially transparent material which is adapted to become opaque upon contact with a photographic aqueous alkaline processing composition, said opacification layer being positioned on the side of the transparent support opposite that which carries the photosensitive system.

20. A photosensitive element as defined in claim 19 wherein said photosensitive system comprises a blue sensitive silver halide emulsion layer in association with a yellow dye developer layer, a green sensitive silver halide emulsion layer in association with a magenta dye developer layer and a red sensitive silver halide emulsion layer in association with a cyan dye developer layer.

21. A photosensitive element as defined in claim 20 further including, on the side of said support which carries said photosensitive system, a reflective layer adapted to the viewing thereagainst of a photographic image in said image receiving layer.

22. A photosensitive element as defined in claim 18 wherein X represents the nonmetallic atoms which complete a tetrazole ring.

23. A photographic element as defined in claim 22 wherein PHOTO is

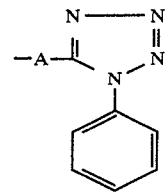

24. A photographic element as defined in claim 23 wherein A is sulfur and $R_2$ or $R_3$ is alkyl.

25. A photographic element comprising a support and at least one layer thereon containing a silver halide emulsion having associated therewith a compound represented by the formula

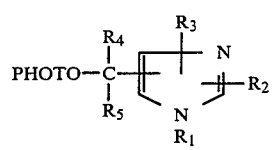

wherein

R is hydrogen, a hydrolyzable group or a group which is cleavable in aqueous alkaline environment;

$R_2$ and $R_3$ are the same or different and are hydrogen, a substituent which modifies a property of said compound, or, when

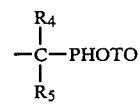

is attached to the 2-position, taken together form a five or six member carbocyclic or heterocyclic ring;

$R_4$ and $R_5$ are the same or different and are hydrogen or alkyl; and

PHOTO is a moiety represented by the formula

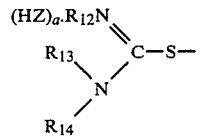

wherein $R_{12}$ and $R_{13}$ and $R_{14}$ are the same or different and are hydrogen or alkyl, Z is a photographically acceptable anion and a is 0, 1 or 2.

26. A photographic product for use in forming a multicolor diffusion transfer image comprising a photosensitive element comprising a support carrying a blue-sensitive silver halide emulsion having a yellow dye developer associated therewith, a green-sensitive silver halide emulsion having a magenta dye developer associated therewith and a red-sensitive silver halide emulsion having a cyan dye developer associated therewith, a second sheet-like element positioned in superposed or superposable relationship with said photosensitive element, an image receiving layer positioned in one of said elements, a rupturable container releasably holding an aqueous alkaline processing composition adapted, when distributed between a pair of predetermined layers carried by said photosensitive element and said second element, to develop said silver halide emulsions and provide a multicolor diffusion transfer image on said image-receiving layer, at least one of said photosensitive and said second elements including a compound represented by the formula

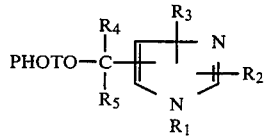

wherein $R_1$ is hydrogen, a hydrolyzable group or a group which is cleavable in aqueous alkaline environment;

$R_2$ and $R_3$ are the same or different and are hydrogen, a substituent which modifies a property of said compound, or, when

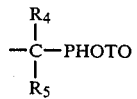

is attached to the 2-position, taken together form a five or six member carbocyclic or heterocyclic ring; $R_4$ and $R_5$ are the same or different and are hydrogen or alkyl; and PHOTO is a moiety represented by the formula

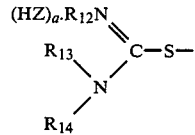

wherein $R_{12}$, $R_{13}$ and $R_{14}$ are the same or different and are hydrogen or alkyl, Z is a photographically acceptable anion and a is 0, 1 or 2.

* * * * *